(12) United States Patent
Wright et al.

(10) Patent No.: US 7,521,474 B2
(45) Date of Patent: Apr. 21, 2009

(54) BIOLOGICALLY ACTIVE LASONOLIDE COMPOUNDS

(75) Inventors: Amy E. Wright, Fort Pierce, FL (US); Shirley A. Pomponi, Ft. Pierce, FL (US); Peter J. McCarthy, Vero Beach, FL (US); Ying Chen, Brevard, NC (US); Ross E. Longley, Tallahassee, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 172 days.

(21) Appl. No.: 11/494,229

(22) Filed: Jul. 27, 2006

(65) Prior Publication Data

US 2006/0264499 A1    Nov. 23, 2006

Related U.S. Application Data

(63) Continuation of application No. 10/875,670, filed on Jun. 23, 2004, now Pat. No. 7,115,756.

(60) Provisional application No. 60/482,215, filed on Jun. 23, 2003.

(51) Int. Cl.
*A61K 31/335*  (2006.01)
*C07D 325/04*  (2006.01)
*C07D 493/12*  (2006.01)

(52) U.S. Cl. .................. 514/450; 514/452; 549/267
(58) Field of Classification Search ............... 549/267; 514/450, 452
See application file for complete search history.

(56) References Cited

U.S. PATENT DOCUMENTS 5,478,861 A    12/1995 Horton et al.
5,684,036 A    11/1997 Horton et al.
5,869,038 A    2/1999  Leifert et al.
6,476,065 B2   11/2002 Gunasekera et al.

OTHER PUBLICATIONS

Barrand, M., Bagrij, T., and Neo, S., Multidrug Resistance- Associated Protein: A Protein Distance from P-glycoprotein Involved in Cytotoxic Drug Expulsion, General Pharmacology (1997), 28 (5): 639-645.
Bellamy, W. T., P-glycoproteins and Multidrug Resistance, Annu. Rev. Pharmacol. Toxicol. (1996), 36: 161-183.
Broxterman, H. J., Giaccone, G., and Lankelma, J., Multidrug resistance proteins and other drug transport-related resistance to natural product agents, Current Opinion in Oncology (1995), 7:532-540.
Casazza, A. M. and C. R. Fairchild (1996) "Paclitaxel (Taxol®): mechanisms of resistance" *Cancer Treat Res.* 87:149-171.
Komarov, P. G., Shtil, A. A., Holian, O. Tee, L., Buckingham, L., Mechetner, E. B., Roninson, I. B., and Coon, J. S., Activation of the *LRP* (Lung Resistance-Related Protein) Gene by Short-Term Exposure of Human Leukemia Cells to Phorbol Ester and Cytarabine, Oncology Research (1998), 10:185-192.
Krishan, A., Fitz, C. M., and Andritsch, I., Drug Retention, Efflux, and Resistance in Tumor Cells, Cytometry (1997), 29:279-285.
Kruh, G. D., Gaughan, K. T., Godwin, A., and Chan, A., Expression Pattern of MRP in Human Tissues and Adult Solid Tumor Cell Lines, Journal of the National Cancer Institute (1995), 87 (16): 1256-1258.
Miller, D. W., Fontain, M., Kolar, C., and Lawson, T., The expression of multidrug resistance-associated protein (MRP) in pancreatic adenocarcinoma cell lines, Cancer Letters (1996), 107:301-306.
Sugawara, I., 1995 "Multidrug Resistance: Role of Multidrug Resistance-Associated Protein (MRP)" *The Cancer Journal* 8(2):59-61.

*Primary Examiner*—Janet L. Andres
*Assistant Examiner*—Raymond Covington
(74) *Attorney, Agent, or Firm*—Saliwanchik, Lloyd & Saliwanchik

(57) ABSTRACT

The subject invention provides novel compositions of biologically active macrolide compounds which can advantageously be used in blocking cellular proliferation, treatment of cancer, treatment of fungal infections and control of spoilage of food, cosmetic and other consumer items.

29 Claims, No Drawings

BIOLOGICALLY ACTIVE LASONOLIDE COMPOUNDS

CROSS-REFERENCE TO A RELATED APPLICATION

This application is a continuation application of application Ser. No. 10/875,670, filed Jun. 23, 2004 now U.S. Pat. No. 7,115,756; which claims the benefit of U.S. provisional application Ser. No. 60/482,215, filed Jun. 23, 2003, in it's entirety.

FIELD OF THE INVENTION

This invention relates to organic compounds and compositions which have useful therapeutic properties. More particularly, the invention concerns novel macrolide compounds having anti-proliferative, antitumor and antifungal activities, pharmaceutical compositions comprising such compounds, and methods of their use for therapeutic purposes and in the control of spoilage of food, cosmetic and other consumer items.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Antiproliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219-1222; Schiff, P. B., J. Fant, S. B. Horwitz [1979] *Nature (London)* 22:665-667). Paclitaxel is also known to have antitumor activity and has undergone a number of clinical trials which have shown it to be effective in the treatment of a wide range of cancers (Rowinski, E. K. R. C. Donehower [1995] *N. Engl. J. Med.* 332:1004-1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978-1983, Vol. I-V; Uemura, D., K. Takahashi, T. Yamamoto, C. Katayama, J. Tanaka, Y. Okumura, Y. Hirata (1985) *J. Am. Chem. Soc.* 107:4796-4798; Minale, L. et al. (1976) *Fortschr. Chem. org. Naturst.* 33:1-72 Faulkner, D. J., *Nat. Prod. Reports* 1984, 1, 251-551; ibid. 1987, 4, 539; ibid 1990, 7, 269; ibid 1993, 10, 497; ibid 1994, 11, 355; ibid 1995, 12, 22; ibid 1998, 15:113-58; ibid 2000 17:1-6; ibid 2000 17: 7-55; ibid 2001, 18: 1-49; 2002, 19: 1-48; Gunasekera, S. P., M. Gunasekera, R. E. Longley and G. K. Schulte (1990) *J. Org. Chem.*, 55:4912-4915.; Horton, P. A., F. E. Koehn, R. E. Longley, and O. J. McConnell, (1994) *J. Am. Chem. Soc.* 116: 6015-6016.

The success of chemotherapy for the treatment of various cancers can be substantially negated though cellular mechanisms which have evolved to enable neoplastic cells to subvert the cytotoxic effects of the drug. Some cells have developed mechanisms, which confer resistance to a number of structurally unrelated drugs. This multi-drug resistance (or MDR) phenomenon may arise through a number of different mechanisms. One of these involves the ability of a cell to reduce intracellular concentrations of a given drug through efflux from cytoplasm through and out the cell membrane by a series of unique ATP-dependent transporter proteins called-P-glycoproteins (Pgp) (Casazza, A. M. and C. R. Fairchild [1996] "Paclitaxel (Taxol®): mechanisms of resistance" *Cancer Treat Res.* 87:149-171). The surface membrane, 170 kDa Pgp, is encoded by the mdr-1 gene and appears to require substrate binding before transport begins. A wide range of compounds including a number of structurally unrelated chemotherapeutic agents (adriamycin, vinblastine, colchicine, etoposide and Taxol), are capable of being transported by Pgp and render the cell resistant to the cytotoxic effects of these compounds. While many normal cell types possess Pgp, in general, tumor cell lines, which possess high levels of mRNA specific for Pgp, also exhibit overexpression of membrane Pgp and demonstrate resistance to various drugs. This intrinsic resistance can be increased multifold by incubation of cells with stepwise increasing doses of a particular drug over a period of several months. This can be further facilitated by the addition of the MDR reversal agent, verapamil (Casazza, A. M. and C. R. Fairchild [1996] supra) in combination with the particular drug. Drug resistant cell lines produced in this fashion exhibit resistance to drug cytotoxicity from 20 to 500 fold, compared to parental cell lines.

An additional target for cancer drug discovery is a high molecular weight membrane protein associated with multi-drug resistance properties of certain tumor cells known as the multidrug resistance-associated protein (MRP). MRP is a 190 kD membrane-bound glycoprotein (Bellamy, W. T. [1996], *Annu. Rev. Pharmacol. Toxicol.*, 36: 161-183.) which belongs to the same family of proteins as the p-glycoprotein pump P-gp (Broxterman, H. J., Giaccone, G., and Lankelma, J. [1995], Current Opinion in Oncology, 7:532-540.) but shares less than 15% homology of amino acids with P-gp (Komorov, P. G., Shtil, A. A., Holian, O., Tee, L., Buckingham, L., Mechetner, E. B., Roninson, I. B., and Coon, J. S. [1998], Oncology Research, 10: 185-192.). MRP has been found to occur naturally in a number of normal tissues, including liver, adrenal, testis, and peripheral blood mononuclear cells (Krishan, A., Fitz, C. M., and Andritsch, I. [1997], Cytometry, 29: 279-285). MRP has also been identified in tissues of the lung, kidney, colon, thyroid, urinary bladder, stomach, spleen (Sugawara, I. [1998] The Cancer Journal, 8(2) and skeletal muscle (Kruh, G. D., Gaughan, K. T., Godwin, A., and Chan, A. [1995], Journal of the National Cancer Institute, 87(16): 1256-1258.). High levels of MRP have been implicated in multidrug resistance (MDR) in cancers of the lung and pancreas (Miller, D. W., Fontain, M., Kolar, C., and Lawson, T. [1996]. Cancer Letters, 107: 301-306.), and in neuroblastomas, leukemias and cancer of the thyroid (Kruh, G. D., Gaughan, K. T., Godwin, A., and Chan, A. [1995], Journal of the National Cancer Institute, 87(16): 1256-1258.), as well as bladder, ovarian and breast cancers (Barrand, M., Bagrij, T., and Neo, S. [1997]., General Pharmacology, 28(5): 639-645.). MRP-mediated MDR involves some of the same classes of compounds as those which are mediated by P-gp, including vinca alkaloids, epipodophyllotoxins, anthracyclins and actinomycin D (Barrand, M., Bagrij, T., and Neo, S. [1997]., General Pharmacology,28(5):

639-645). However, the substrate specificity has been demonstrated to differ from that of P-gp (Komorov, P. G., Shtil, A. A., Holian, O., Tee, L., Buckingham, L., Mechetner, E. B., Roninson, I. B., and Coon, J. S. [1998], Oncology Research, 10: 185-192.). Drugs which would inhibit or which are not substrates for the MDR pump would, therefore, be useful as chemotherapeutic agents.

Of further significant importance to man is the control of fungi which can cause human, animal and plant diseases as well as food spoilage. Considerable research and resources have been devoted to identifying antifungal agents. While certain methods and chemical compositions have been developed which aid in inhibiting or controlling the growth of fungi, new methods and antifungal compositions are needed.

Human mycotic infections may be grouped into superficial, subcutaneous, and deep (or systemic) mycoses. Superficial fungal infections of skin, hair and nails may be chronic and resistant to treatment but rarely affect the general health of the patient. Deep mycoses, on the other hand, may produce systemic involvement and are sometimes fatal.

The deep mycoses are caused by organisms that live free in nature in soil or on decaying organic material and are frequently limited to certain geographic areas. In such areas, many people acquire the fungal infection. A majority develop only minor symptoms or none at all, and only a small minority of infections progress to full-blown serious or fatal disease. The host's cell-mediated immune reactions are of paramount importance in determining the outcome of such infections.

Post-harvest losses during storage of plant produce are caused, interalia, by fungal and bacterial pathogens. Fungicidal compounds have long been used to increase yields and extend agricultural production capabilities into new areas. They have also been extremely important tools for ameliorating season-to-season differences in yield and quality caused by weather-driven variations in disease pressure.

Chemical fungicides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling fungi.

One example of the need to control post-harvest spoilage of agriculture products pertains to green and blue molds of citrus fruits caused by *Penicillium digitatum* and *P. italicum*. These molds cause severe damage during storage and shipping. The existing fresh-market industry relies completely on a combination of several chemical treatments to deliver sound fruit to distant markets over substantial periods of time without excessive damage caused by these molds. Unfortunately, there are increasing concerns about the safety of the chemicals currently used to control these fungal pathogens. Also, there are increasing problems with fungal strains with resistance to the most effective compounds.

In another example, powdery mildew of grapes caused by *Uncinula necator* can cause severe damage even in dry areas such as California. Traditionally this disease was controlled with applications of elemental sulfur, but this necessitates frequent, high volume applications of an irritating material. The introduction of ergosterol biosynthesis inhibiting fungicides (primarily triazoles) greatly simplifies control, but also selects for tolerant strains. Some of these compounds are also known to have potential teratogenic effects and very long soil residuals. In these and other examples, alternative control methods are in great demand—particularly methods which are safer or more environmentally benign.

To prevent fungal spoilage it is common practice in many countries to spray produce with systemic fungicides in the field and to dip harvested produce in fungicide solutions prior to storage. Since the oncogenic nature of many of the most commonly used fungicides is increasingly recognized and because the persistence of most fungicides is increased by the low storage temperatures the postharvest use of fungicides is of growing concern.

Additionally, resistance to the fungicides, used has been reported and suppression of the main spoilage organism *B. cinera* by fungicides such as BENOMYL fungicide has been shown to result in increased population of *A. brassicicola* which causes a more penetrating rot of produce than *B. cinera*. See, for example, U.S. Pat. No. 5,869,038.

The future role of fungicides in agriculture is increasingly threatened by several factors including; the development of pest resistance, increasing concerns about food safety and environmental accumulation of toxic compounds. As older fungicides are removed from the market due to regulatory changes there is an increasing need to find new effective fungicidal compounds.

Lasonolides and other macrolides have previously been found to possess useful biological activities. See, for example, U.S. Pat. Nos. 5,478,861; 5,684,036; and 6,476,065.

BRIEF SUMMARY OF THE INVENTION

The subject invention provides novel compositions of biologically active compounds that have utility for use in inhibiting cellular proliferation. In a specific embodiment, the compounds and compositions of the subject invention can be used in the treatment of cancer. In one embodiment, the compounds are used to treat multidrug resistant cancers. The compounds and compositions of the subject invention can also be used in the control of fungal growth.

In one embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

In a further specific embodiment, the novel compositions and methods of the subject invention subject can be used in the control of fungal growth. Because of the biological activity of these compounds, they can be used for treatment of plant and animal fungal infections, to prevent spoilage of organic compositions such as food and cosmetics, and as disinfectants. In a preferred embodiment, the novel compounds, compositions and methods of use of the subject invention can advantageously be used to inhibit the growth of fungi in a mammalian host. As used herein, reference to "antifungal activity" includes fungicidal and fungistatic activity as well as the inhibition of fungal germination or growth.

In specific embodiments, the subject invention provides the novel compounds Lasonolides C (I), D (II), E (III) and F (IV).

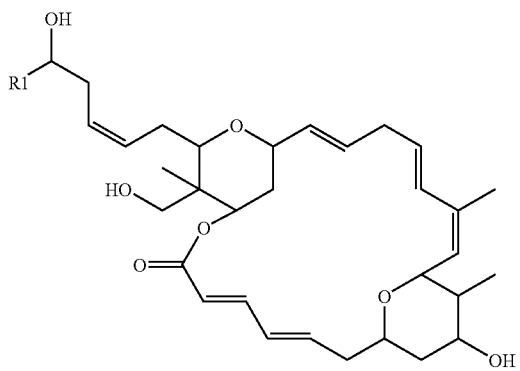

(I) Lasonolide C R₁=

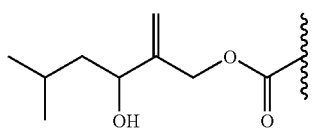

(II) Lasonolide D R₁=H
(III) Lasonolide E R₁=COOCH₂CH₃
(IV) Lasonolide F R₁=COOH Lasonolides C-F have not been isolated previously from a natural source nor have they been previously synthesized.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

The subject invention provides novel compositions of biologically active macrolide compounds which are useful for inhibiting pathological cellular proliferation. Advantageously, the macrolide compounds of the subject invention can be used to inhibit unwanted cellular proliferation, including the pathogenic proliferation of tumor and fungal cells.

In a preferred embodiment, these compounds can be used for treating cancer. More specifically, the novel compounds, compositions and methods of use can advantageously be used to inhibit the growth of tumor and other cancer cells in a mammalian host. As described herein, the compounds of the subject invention have utility for use in the treatment of cancer. More particularly, the subject compounds can be used for inhibiting in a human the growth of tumor cells, including cells of breast, prostate, colon, CNS, ovarian, renal, liver, pancreatic, uterine, or lung tumors, as well as human leukemia or melanoma cells. The compounds also have utility in the treatment of multi-drug resistant cancer cells.

The subject invention further provides novel compositions of biologically active macrolide compounds which are useful in the control of fungal growth. Because of the biological activity of these compounds, they can be used for treatment of plant and animal fungal infections, to prevent spoilage of organic compositions such as food and cosmetics, and as disinfectants. In a preferred embodiment, the novel compounds, compositions and methods of use of the subject invention can advantageously be used to inhibit the growth of fungi in a mammalian host. As used herein, reference to "antifungal activity" includes fungicidal and fungistatic activity as well as the inhibition of fungal germination or growth.

In a preferred embodiment, the subject invention provides compounds having the following formula:

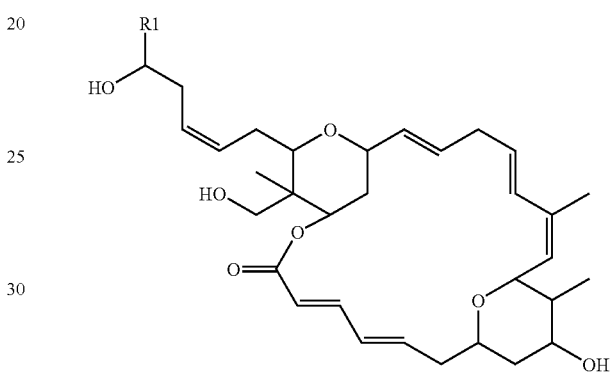

Wherein R1=

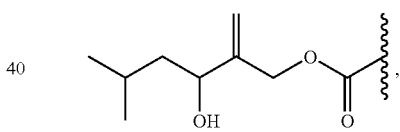

H, COOCH₂CH₃, or COOH

In a specific embodiment, the subject invention provides compounds having the following formula:

(I)

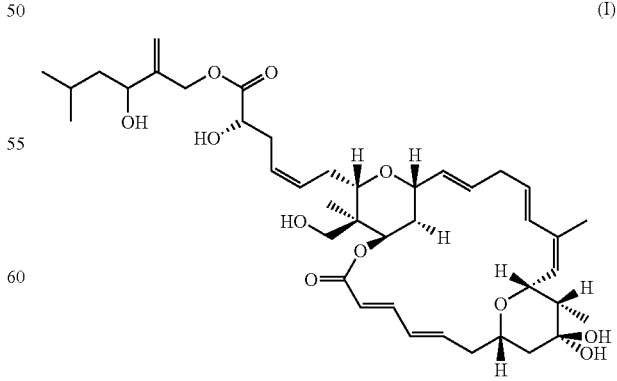

In a further specific embodiment, the subject invention provides compounds having the following formula:

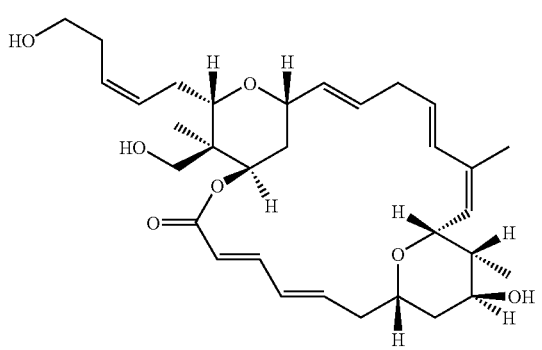

(II)

In a further specific embodiment, the subject invention provides compounds having the following formula:

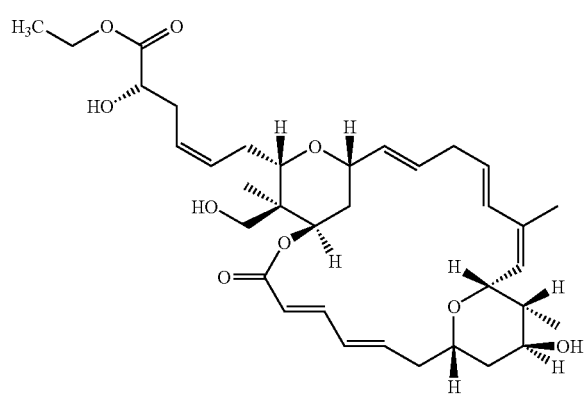

(III)

In a further specific embodiment, the subject invention provides compounds having the following formula:

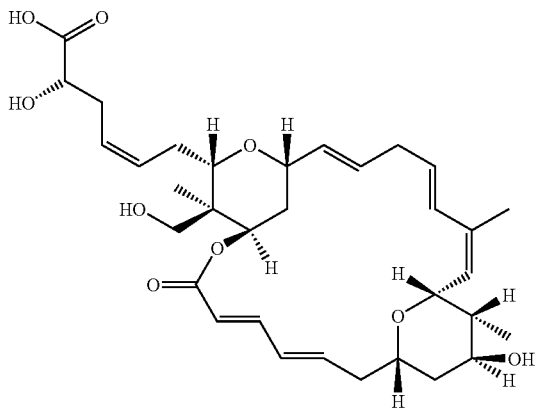

(IV)

The subject invention further pertains to isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

In accordance with the subject invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells including multi-drug resistant cancer cells.

In preferred embodiments of the invention, the compounds are substantially pure, i.e., contain at least 95% of the compound as determined by established analytical methods.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

As used in this application, the terms "analogs," refers to compounds which are substantially the same as another compound but which may have been modified by, for example, adding or removing side groups.

The scope of the invention is not limited by the specific examples and suggested procedures and uses related herein since modifications can be made within such scope from the information provided by this specification to those skilled in the art.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Isolation and Structure Elucidation of Lasonolides C(I), D (II) E (III) and F (IV)

A. Collection and Taxonomy of the Source Organism

A sample of Forcepia triabilis (Phylum: Porifera, Class Demospongiae, Order Poecilosclerida, Family: Myxillidae) was collected by manned submersible at a depth of 70.7 m in the Gulf of Mexico, 100 nmi West of Naples Fla. (latitude 26° 15.98'N, longitude 83° 42.58'W). The sponge morphology is spherical with fat fingers protruding from the top. It is compressible and is red-orange in color both external and internal. The sponge corresponds most closely to the species triabilis as described by Van Soest R. W. M. (1984) "Marine Sponges from Curacao and other Caribbean localities. Part III Poecilosclerida." Stud. Fauna Curacao Caribb. Isl. 66(199)1-167. A reference sample preserved in ethanol has been deposited in the Harbor Branch Oceanographic Museum (catalog number 003:01005, DBMR number 11-VIII-99-2-001) and is available for taxonomic evaluation by those skilled in the art.

B. Isolation and Structure Elucidation of Lasonolides C(I), D (II), E (III) and F (IV).

Isolation of lasonolides C, D, E, and F.

The frozen sponge (3.94 kg wet wt) was diced and extracted exhaustively with $CH_3CH_2OH$ (Pharmco 100%). The combined $CH_3CH_2OH$ extracts were concentrated to dryness (86.5 g) and the residue partitioned between ethyl acetate and water. The ethyl acetate partition was concentrated to dryness to yield 5.3 g of an orange oil. 1.7 g of the residue from the ethyl acetate partition was chromatographed by vacuum flash chromatography on a custom prepared RP-18 stationary phase using a step gradient of $H_2O$—$CH_3CN$—$CH_3OH$—$CH_2Cl_2$ as eluent. Column size was 360 mL.

The eluent series is as follows: fraction 1, 800 mL of $H_2O$—$CH_3CN$ (80:20 v/v); fraction 2, 800 mL of $H_2O$—$CH_3CN$ (50:50 v/v); fraction 3, 800 mL of $H_2O$—$CH_3CN$ (20:80 v/v); fraction 4, 800 mL of $CH_3CN$; fraction 5, 500 mL of MeOH—$CH_2Cl_2$ (1:1 v/v).

The column was repeated on a second 1.7 g portion of the EtOAc partition and similar fractions from the two columns were combined prior to further purification.

Fraction 1 (139.8 mg) was further purified by reversed-phase HPLC [Vydac Protein and Peptide C18 column, 10×250 mm, 10μ particle size, Solvent A: 5% $CH_3CN$ in water v/v; Solvent B: 100% $CH_3CN$; t=0 minutes, A:B (85: 15); t=10 minutes, A:B (80:20); t=20 minutes, A:B (70:30); t=25 minutes, A: B (0:100); t=35 minutes, A: B (0:100); flow=3 mL/min; Detected by uv absorption observed at 230 nm] to yield 8.6 mg of lasonolide F (retention time=17.05 minutes).

Fraction 2 (314.5 mg) was further purified by reversed-phase HPLC [Vydac Protein and Peptide C18 column, 10×250 mm, 10μ particle size, Solvent A: 5% $CH_3CN$ in water v/v; Solvent B: 100% acetonitrile; t=0 minutes, A:B (70:30); t=25 minutes, A:B (25:75); t=30 minutes, A:B (0:100); t=35 A:B (0:100); flow=3 mL/min; Detected by uv absorption observed at 230 nm] to yield 48.9 mg of lasonolide C (retention time=16.75 minutes), 9.5 mg of lasonolide D (retention time=11.96 minutes), and 11.4 mg of lasonolide E (retention time=14.01 minutes).

Lasonolide C (I): white powder; MS: m/z observed 713.42727, calculated 713.42647 Δ=−0.8 mmu for formula $C_{41}H_{61}O_{10}$ (M+H$^+$); See Table 1 for $^1H$ and $^{13}C$ NMR data.

Lasonolide D (II): white powder; See Table 2 for $^1H$ and $^{13}C$ NMR data.

Lasonolide E (III): white powder; MS: m/z observed 637.3390, calculated 637.3352 Δ=3.8 mmu for formula $C_{35}H_{51}O_9$ (M+H$^+$); See Table 3 for $^1H$ and $^{13}C$ NMR data.

Lasonolide F (IV): colorless oil. See Table 4 for $^1H$ and $^{13}C$ NMR data.

Please note that the numbering of the atoms in the following tables is based on the system shown below:

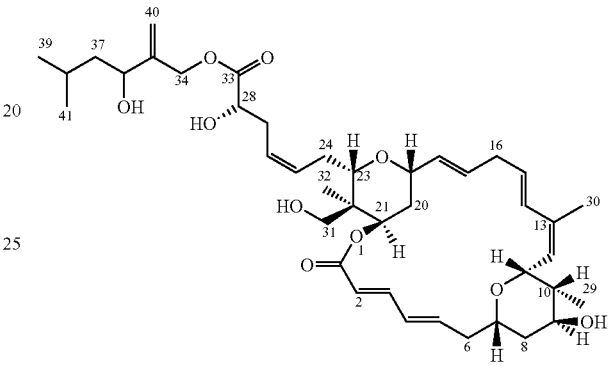

Numbering system for the lasonolides

TABLE 1

NMR Spectral data for Lasonolide C (I)
Lasonolide C (in CDCL3)

| Atom No. | $^{13}C$ NMR (mult) | $^1H$ NMR δ (mult., J Hz) |
|---|---|---|
| 1 | 168.52 s | — |
| 2 | 118.25 d | 5.69(d, J=15.5) |
| 3 | 148.33 d | 7.24(dd, J=15.5, 11.0) |
| 4 | 128.96 d | 6.26(dd, J=15.0, 11.0) |
| 5 | 145.17 d | 6.15(dt, J=15.0, 6.0) |
| 6 | 38.51 t | 2.35(2H, m) |
| 7 | 72.46 d | 4.05(m) |
| 8 | 33.75 t | 1.66(m) and 1.51(m) |
| 9 | 70.38 d | 3.96(m) |
| 10 | 38.22 d | 1.64(m) |
| 11 | 68.90 d | 4.82(dd, J=9.5, 1.7) |
| 12 | 124.59 d | 5.46(d, J=9.3) |
| 13 | 138.83 s | — |
| 14 | 129.13 d | 6.59(d, J=15.7) |
| 15 | 129.60 d | 5.81(dt, J=15.7, 7.5) |
| 16 | 33.61 t | 2.89(dd, J=12.5, 7.5) and 2.71(m) |
| 17 | 128.81 d | 5.51(m) |
| 18 | 134.28 d | 5.51(m) |
| 19 | 77.14 d | 4.30(m) |
| 20 | 34.89 t | 1.87(dt, J=13.0, <1) and 1.40(m) |
| 21 | 74.68 d | 4.94(brs) |
| 22 | 41.20 s | — |
| 23 | 77.98 d | 3.56(dd, J=9.6, 2.2) |
| 24 | 28.06 t | 2.22(m) and 2.07(m) |
| 25 | 130.84 d | 5.68(dd, J=10.5, 7.5) |
| 26 | 125.03 d | 5.49(m) |
| 27 | 32.48 t | 2.50(m) |
| 28 | 70.64 d | 4.23(m) |
| 29 | 11.36 q | 1.03(d, J=7.0) |
| 30 | 21.04 q | 1.80(s) |
| 31 | 65.58 t | 3.39(d, J=11.5) and 3.32(d, J=11.5) |
| 32 | 15.12 q | 1.08(s) |
| 33 | 173.94 s | — |
| 34 | 64.75 t | 4.76(d, J=13.0) and 4.71(d, J=13.0) |

TABLE 1-continued

NMR Spectral data for Lasonolide C (I)
Lasonolide C (in CDCL3)

| Atom No. | $^{13}$C NMR (mult) | $^{1}$H NMR δ (mult., J Hz) |
|---|---|---|
| 35 | 146.22 s | — |
| 36 | 71.44 d | 4.24(m) |
| 37 | 44.63 t | 1.49(m) and 1.36(m) |
| 38 | 24.63 t | 1.74(m) |
| 39 | 22.03 q | 0.93(d, J=6.5) |
| 40 | 113.94 t | 5.24(s) and 5.15(s) |
| 41 | 23.17 q | 0.93(d, J=6.5) |

TABLE 2

NMR Spectral data for Lasonolide D (II)
Lasonolide D (in CDCl3)

| Atom No. | $^{13}$C NMR (mult) | $^{1}$H NMR δ (mult., J Hz) |
|---|---|---|
| 1 | 168.53 s | — |
| 2 | 118.39 d | 5.71(d, J=15.5) |
| 3 | 148.29 d | 7.24(dd, J=15.5, 11.0) |
| 4 | 129.05 d | 6.26(dd, J=15.0, 11.0) |
| 5 | 145.08 d | 6.16(dt, J=15.0, 6.0) |
| 6 | 38.55 t | 2.36(m) |
| 7 | 72.49 d | 4.06(m) |
| 8 | 33.81 t | 1.68(m) and 1.53(m) |
| 9 | 70.78 d | 3.99(m) |
| 10 | 38.37 d | 1.60(m) |
| 11 | 68.95 d | 4.81(dd, J=9.4, 1.8) |
| 12 | 124.58 d | 5.46(d, J=9.4) |
| 13 | 138.94 s | — |
| 14 | 129.14 d | 6.58(d, J=16) |
| 15 | 129.74 d | 5.82(dt, J=16, 7.5) |
| 16 | 33.69 t | 2.90(m) and 2.76(m) |
| 17 | 128.87 d | 5.50(m) |
| 18 | 134.20 d | 5.50(m) |
| 19 | 77.17 d | 4.32(dd, J=11, 7.0) |
| 20 | 35.05 t | 1.86(t, J=13.0) |
| 20 | | 1.42(m) |
| 21 | 74.77 d | 4.96(brs) |
| 22 | 41.26 s | — |
| 23 | 77.82 d | 3.59(d, J=10.5) |
| 24 | 28.02 t | 2.33(m) and 2.04(m) |
| 25 | 130.02 d | 5.62(dd, m) |
| 26 | 127.81 d | 5.50(m) |
| 27 | 30.72 t | 2.44(m) and 2.25(m) |
| 28 | 61.85 t | 3.67(dt, J=10.5, 5) and 3.58(m) |
| 29 | 11.42 q | 1.06(d, J=7.0) |
| 30 | 21.10 q | 1.82(s) |
| 31 | 65.74 t | 3.43(d, J=11.5) and 3.34(d, J=11.5) |
| 32 | 15.30 q | 1.12(s) |

TABLE 3

NMR Spectral data for Lasonolide E (III)
Lasonolide E (CDCl3)

| Atom No. | $^{13}$C NMR δ mult. | $^{1}$H NMR δ (mult., J Hz) |
|---|---|---|
| 1 | 168.55 s | — |
| 2 | 118.34 d | 5.71(d, J=15.5) |
| 3 | 148.32 d | 7.24(dd, J=15.5, 10.5) |
| 4 | 129.01 d | 6.26(dd, J=15.0, 11.0) |
| 5 | 145.10 d | 6.15(dt, J=15.0, 6.0) |
| 6 | 38.52 t | 2.36(m) |
| 7 | 72.48 d | 4.06(m) |
| 8 | 33.80 t | 1.67(m) and 1.53(m) |
| 9 | 70.76 d | 3.99(m, J=2.5) |
| 10 | 38.32 d | 1.64(m) |
| 11 | 68.93 d | 4.81(d, J=9.5) |
| 12 | 124.58 d | 5.46(d, J=9.5) |
| 13 | 138.91 s | — |

TABLE 3-continued

NMR Spectral data for Lasonolide E (III)
Lasonolide E (CDCl3)

| Atom No. | $^{13}$C NMR δ mult. | $^{1}$H NMR δ (mult., J Hz) |
|---|---|---|
| 14 | 129.14 d | 6.59(d, J=16) |
| 15 | 129.69 d | 5.83(dt, J=16, 7.0) |
| 16 | 33.67 t | 2.90(dt, J=13.5, 7.0) and 2.75(m) |
| 17 | 129.01 d | 5.52(m) |
| 18 | 134.16 d | 5.50(m) |
| 19 | 77.08 d | 4.32(m) |
| 20 | 34.98 t | 1.88(t, J=13.0) and 1.42(m) |
| 21 | 74.72 d | 4.96(brs) |
| 22 | 41.26 s | — |
| 23 | 78.03 d | 3.56(dd, J=10, 2.5) |
| 24 | 28.07 t | 2.20(m) and 2.04(m) |
| 25 | 130.77 d | 5.68(dd, J=10.5, 7.5) |
| 26 | 125.05 d | 5.50(m) |
| 27 | 32.50 t | 2.50(2H, m) |
| 28 | 70.25 d | 4.20(dd, J=6.5, 4.5) |
| 29 | 11.40 q | 1.06(d, J=7.0) |
| 30 | 21.08 q | 1.82(s) |
| 31 | 65.66 t | 3.41(d, J=11.5) and 3.33(d, J=11.5) |
| 32 | 15.18 q | 1.12(s) |
| 33 | 174.29 s | — |
| 34 | 61.47 t | 4.23(2H, q, J=7.0) |
| 35 | 14.22 q | 1.30(3H t, J=7.0) |

TABLE 4

NMR Spectral data for Lasonolide F (IV)
Lasonolide F (in d4-methanol)

| Atom No. | $^{13}$C NMR δ mult. | $^{1}$H NMR δ (mult., J Hz) |
|---|---|---|
| 1 | 169.05 s | — |
| 2 | 120.72 d | 5.75(d, J=15.2) |
| 3 | 148.02 d | 7.27(dd, J=15.2, 9.7) |
| 4 | 130.54 d* | 6.26(dd, J=15.0, 9.5) |
| 5 | 145.44 d | 6.22(dt, J=15.0, 4.5) |
| 6 | 40.46 t | 2.22(m) |
| 7 | 74.62 d | 4.01(t, J=11) |
| 8 | 34.86 t | 1.63(m) and 1.47(m) |
| 9 | 71.39 d | 3.84(m) |
| 10 | 39.08 d | 1.58(m) |
| 11 | 70.45 d | 4.81(dd, J=10, 2.5) |
| 12 | 125.90 d | 5.40(d, J=9.4) |
| 13 | 139.67 s | — |
| 14 | 130.62 d* | 6.62(d, J=15.9) |
| 15 | 130.89 d* | 5.84(dt, J=15.9, 8.0) |
| 16 | 34.58 t | 2.80(m) and 2.68(m) |
| 17 | 130.10 d* | 5.52(m) |
| 18 | 135.97 d | 5.50(dd, J=10.3, 4.8) |
| 19 | 78.62 d | 4.21(t, J=10.3) |
| 20 | 35.16 t | 1.81(dd, J=12.5, 5) and 1.29(m) |
| 21 | 75.29 d | 5.01(brs) |
| 22 | 41.80 s | — |
| 23 | 80.90 d | 3.65(dd, J=10, 2.5) |
| 24 | 29.39 t | 2.30(m) and 2.04(m) |
| 25 | 130.28 d* | 5.58(m) |
| 26 | 127.68 d | 5.50(m) |
| 27 | 34.15 t | 2.50(m) and 2.30(m) |
| 28 | 73.16 d | 3.90(dd, J=6.7, 4.2) |
| 29 | 11.66 q | 0.99(d, J=7.4) |
| 30 | 20.99 q | 1.80(s) |
| 31 | 66.09 t | 3.40(d, J=11.0) and 3.43(d, J=11.0) |
| 32 | 15.42 q | 1.04(s) |
| 33 | 180.50 s | — |

EXAMPLE 2

Antitumor Effects of Lasonolides C (I), D (II) and E (III)

The lasonolide compounds were analyzed as to their effects on proliferation of A549 human lung adenocarcinoma, PANC-1 human pancreatic cancer and NCI-ADR-RES tumor cell lines. A549 human lung adenocarcinoma, PANC-1 pancreatic cancer cells and the NCI/ADR-RES (formerly MCF-7/ADR) human breast cell lines were obtained from the American Type Culture Collection (Rockville, Md.).

All cell lines are maintained in Roswell Park Memorial Institute (RPMI) medium 1640 supplemented with 100 U/mL penicillin 100 μg/ml streptomycin, 60 μg/ml L-glutamine, 18 mM HEPES, 0.05 mg/mL gentamycin and 10% fetal bovine serum (for the PANC-1 cell line the media is also supplemented with 100 μg/ml sodium pyruvate and 2.5 mg/ml glucose). Cell lines are cultured in plastic tissue culture flasks and kept in an incubator at 37° C. in humidified air containing 5% $CO_2$.

To assess the antiproliferative effects of agents against the various cell lines, 200 μl cultures (96-well tissue culture plates, Nunc, Denmark) are first established at $3 \times 10^4$ cells/ml for adherent lines in tissue culture medium and incubated for 24 hr at 37° C. in 10% $CO_2$ in air in order to allow cells to attach. A volume of 100 μl of medium is removed from each test well and 100 μl of medium containing serial, two-fold dilutions of the test agent is added to each well containing tumor cells. Medium without drug is also added to wells containing tumor cells which serve as no drug controls.

Positive drug controls are included to monitor drug sensitivity of each of the cell lines. These include varying dilutions of 5-fluorouracil, and doxorubicin. After 72-h exposure, tumor cells are enumerated using 3-[4,5-Dimethylthiazol-2-yl]-2,5-diphenyltetrazolium bromide (MTT) (M. C. Alley, et al., Cancer Res. 48:589, 1988) as follows:

A volume of 75 μl of warm growth media containing 5 mg/ml MTT is added to each well, cultures returned to the incubator, and left undisturbed for 3 hours. To spectrophotometrically quantitate formation of reduced formazan, plates are centrifuged (900×g, 5 minutes), culture fluids removed by aspiration, and 200 μl of acidified isopropanol (2 ml concentrated HCl/liter isopropanol) added per well. The absorbance of the resulting solutions is measured at 570 nm with a plate reader (Spectra II (Tecan Laboratories). The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp.316-348, Charles Griffin Co., London, 1978). A linear relationship between tumor cell number and formazan production has been routinely observed over the range of cell densities observed in these experiments. The two standard drug controls (indicated above) are included in each assay to monitor the drug sensitivity of each of the cell lines and $IC_{50}$ values are determined for each drug-cell combination.

A summary of results in these assays for compounds I-III can be found in Table 5.

TABLE 5

Antitumor Activity of New Lasonolides in μg/mL (μM)

|  | A549 $IC_{50}$ μg/mL (μM) | PANC-1 $IC_{50}$ μg/mL (μM) | NCI ADR-RES $IC_{50}$ μg/mL (μM) |
|---|---|---|---|
| Lasonolide C (I) | 0.095 (0.13) | 0.27 (0.38) | 0.8 (1.12) |
| Lasonolide D (II) | 2.4 (4.5) | 2.6 (4.9) | >5 (>9) |
| Lasonolide E (III) | 0.19 (0.31) | 0.35 (0.57) | >5 (>8) |

EXAMPLE 3

Antifungal Activity of Lasonolide C (I) and Lasonolide F (IV)

A. Effects of Lasonolides C and F on In Vitro growth of Candida albicans

The antifungal activity of lasonolides C and F against Candida albicans (American Type Culture Collection strain 44506) was determined through the use of both agar diffusion and broth dilution assays.

Agar diffusion assays were performed using Sabouraud Dextrose agar plates seeded with the test microbe at $10^5$/ml. Disks (6.35 mm, Schliecher and Schuell) were impregnated with 25 μg of test compound, allowed to dry and then placed on the agar surface. After incubation at 37° C. for 24 hours the zones of growth inhibition were determined. A control disk containing 100IU nystatin was run on the same plate as the test compound: the zone of inhibition was 28 mm.

Broth dilution assays were performed as standard 96-well microtiter assays in a total volume of 50 μl with a seeding density of $10^3$ cells/ml. The concentration range for test compound ranged from 50 to 3 μg/ml as two-fold dilutions. Plates were incubated at 37° C. for 24 hours at which time the Minimum Inhibitory Concentration (MIC) was determined as the lowest concentration in the test range that completely inhibited growth of C. albicans. 5-fluorocytosine was used as an antifungal control for the assay: the MIC for 5-fluorocytosine was 0.62 μg/ml.

Results: Lasonolide C (I) shows a growth inhibitory zone of 15 mm when tested at a concentration of 25 μg/ml in the Candida albicans disk diffusion assay. The Minimum inhibitory concentration (MIC) of Lasonolide C (I) against Candida albicans in SDB broth is 5 μg/ml and in RPMI broth is 12.5 μg/ml.

Lasonolide F (IV) shows a growth inhibitory zone of 10 mm when tested at a concentration of 25 μg/ml in the Candida albicans disk diffusion assay. The Minimum inhibitory concentration (MIC) of Lasonolide F (IV) against Candida albicans in SDB broth is 50 μg/ml while in RPMI broth it is greater than 50 μg/ml.

EXAMPLE 4

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting cancer cell proliferation, said method comprising administering to a patient in need of such treatment an effective amount of a compound having the following structure:

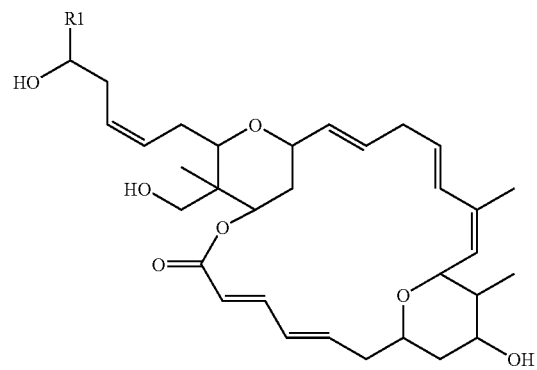

wherein R1=

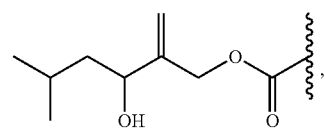

H, COOCH$_2$CH$_3$, or COOH or a salt of said compound.

2. The method, according to claim 1 wherein said compound is selected from the group consisting of (I)

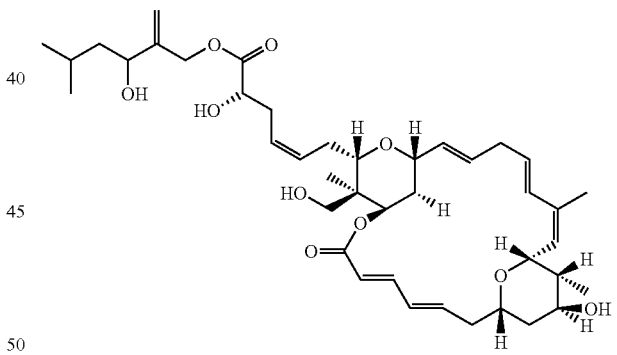

(II)

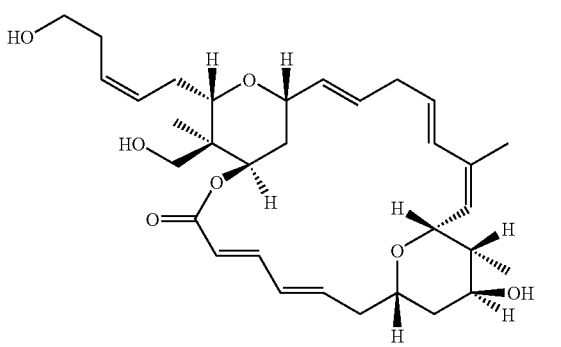

-continued (III)

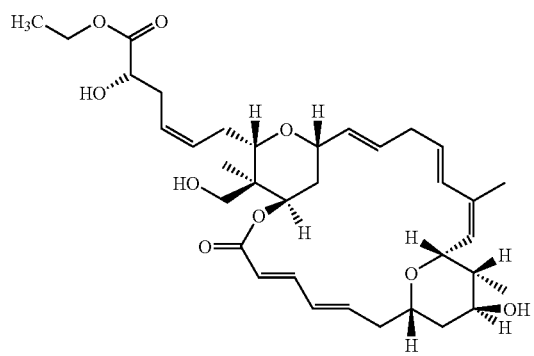

and (IV)

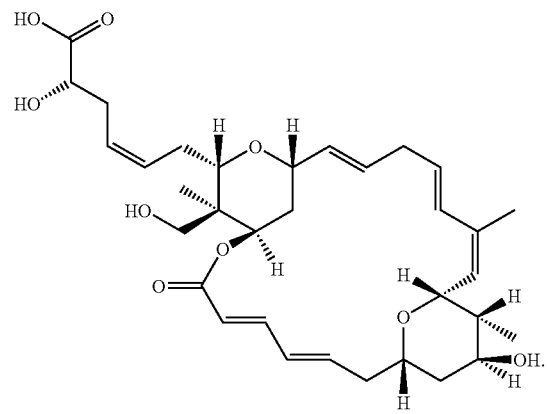

3. The method, according to claim 1, wherein the compound has the following structure:

(I)

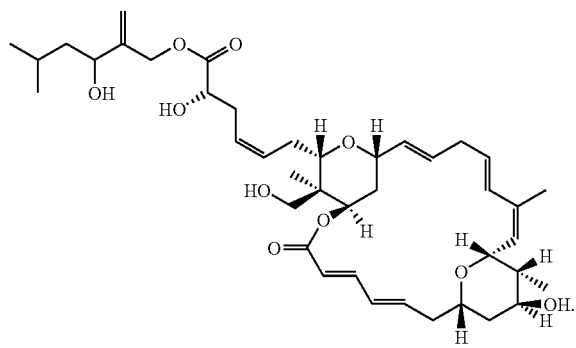

4. The method, according to claim 1 wherein the compound has the following structure:

(II)

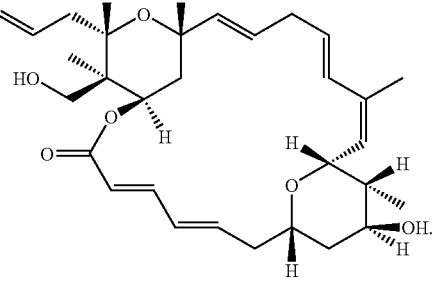

5. The method, according to claim 1, wherein the compound has the following structure:

(III)

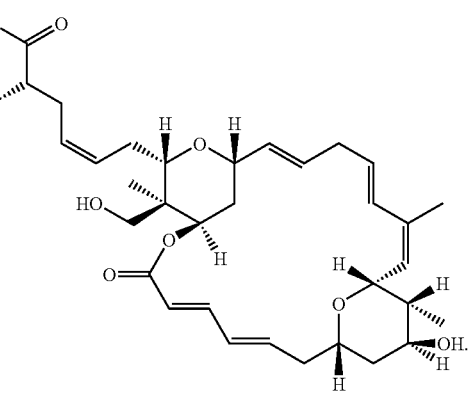

6. The method, according to claim 1, wherein the compound has the following structure:

(IV)

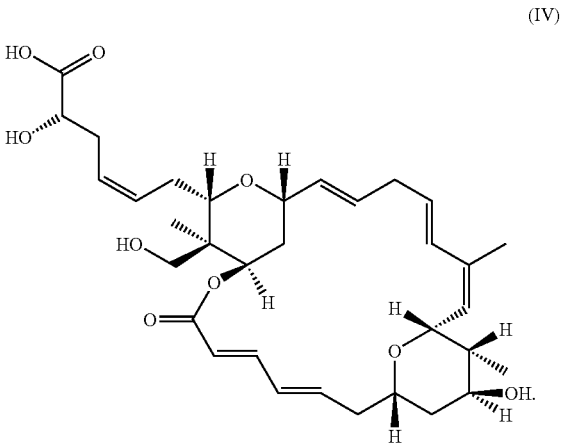

7. The method, according to claim 1, wherein said compound has the following spectroscopic properties:

| Lasonolide C (in CDCL3) | | |
|---|---|---|
| Atom No. | $^{13}$C NMR (mult) | $^1$H NMR δ (mult., J Hz) |
| 1 | 168.52 s | — |
| 2 | 118.25 d | 5.69(d, J=15.5) |
| 3 | 148.33 d | 7.24(dd, J=15.5, 11.0) |
| 4 | 128.96 d | 6.26(dd, J=15.0, 11.0) |
| 5 | 145.17 d | 6.15(dt, J=15.0, 6.0) |
| 6 | 38.51 t | 2.35(2H, m) |
| 7 | 72.46 d | 4.05(m) |
| 8 | 33.75 t | 1.66(m) and 1.51(m) |
| 9 | 70.38 d | 3.96(m) |
| 10 | 38.22 d | 1.64(m) |
| 11 | 68.90 d | 4.82(dd, J=9.5, 1.7) |
| 12 | 124.59 d | 5.46(d, J=9.3) |
| 13 | 138.83 s | — |
| 14 | 129.13 d | 6.59(d, J=15.7) |
| 15 | 129.60 d | 5.81(dt, J=15.7, 7.5) |
| 16 | 33.61 t | 2.89(dd, J=12.5, 7.5) and 2.71(m) |
| 17 | 128.81 d | 5.51(m) |
| 18 | 134.28 d | 5.51(m) |
| 19 | 77.14 d | 4.30(m) |
| 20 | 34.89 t | 1.87(dt, J=13.0, <1) and 1.40(m) |
| 21 | 74.68 d | 4.94(brs) |
| 22 | 41.20 s | — |
| 23 | 77.98 d | 3.56(dd, J=9.6, 2.2) |
| 24 | 28.06 t | 2.22(m) and 2.07(m) |
| 25 | 130.84 d | 5.68(dd, J=10.5, 7.5) |
| 26 | 125.03 d | 5.49(m) |
| 27 | 32.48 t | 2.50(m) |
| 28 | 70.64 d | 4.23(m) |
| 29 | 11.36 q | 1.03(d, J=7.0) |
| 30 | 21.04 q | 1.80(s) |
| 31 | 65.58 t | 3.39(d, J=11.5) and 3.32(d, J=11.5) |
| 32 | 15.12 q | 1.08(s) |
| 33 | 173.94 s | — |
| 34 | 64.75 t | 4.76(d, J=13.0) and 4.71(d, J=13.0) |
| 35 | 146.22 s | — |
| 36 | 71.44 d | 4.24(m) |
| 37 | 44.63 t | 1.49(m) and 1.36(m) |
| 38 | 24.63 d | 1.74(m) |
| 39 | 22.03 q | 0.93(d, J=6.5) |
| 40 | 113.94 t | 5.24(s) and 5.15(s) |
| 41 | 23.17 q | 0.93(d, J=6.5). |

8. The method, according to claim 1, wherein said compound has the following spectroscopic properties:

| Lasonolide D (in CDCl3) | | |
|---|---|---|
| Atom No. | $^{13}$C NMR (mult) | $^1$H NMR δ (mult., J Hz) |
| 1 | 168.53 s | — |
| 2 | 118.39 d | 5.71(d, J=15.5) |
| 3 | 148.29 d | 7.24(dd, J=15.5, 11.0) |
| 4 | 129.05 d | 6.26(dd, J=15.0, 11.0) |
| 5 | 145.08 d | 6.16(dt, J=15.0, 6.0) |
| 6 | 38.55 t | 2.36(m) |
| 7 | 72.49 d | 4.06(m) |
| 8 | 33.81 t | 1.68(m) and 1.53(m) |
| 9 | 70.78 d | 3.99(m) |
| 10 | 38.37 d | 1.60(m) |
| 11 | 68.95 d | 4.81(dd, J=9.4, 1.8) |
| 12 | 124.58 d | 5.46(d, J=9.4) |
| 13 | 138.94 s | — |
| 14 | 129.14 d | 6.58(d, J=16) |
| 15 | 129.74 d | 5.82(dt, J=16, 7.5) |
| 16 | 33.69 t | 2.90(m) and 2.76(m) |
| 17 | 128.87 d | 5.50(m) |
| 18 | 134.20 d | 5.50(m) |
| 19 | 77.17 d | 4.32(dd, J=11, 7.0) |
| 20 | 35.05 t | 1.86(t, J=13.0) |
| 20 | | 1.42(m) |
| 21 | 74.77 d | 4.96(brs) |

| Lasonolide D (in CDCl3) | | |
|---|---|---|
| Atom No. | $^{13}$C NMR (mult) | $^1$H NMR δ (mult., J Hz) |
| 22 | 41.26 s | — |
| 23 | 77.82 d | 3.59(d, J=10.5) |
| 24 | 28.02 t | 2.33(m) and 2.04(m) |
| 25 | 130.02 d | 5.62(dd, m) |
| 26 | 127.81 d | 5.50(m) |
| 27 | 30.72 t | 2.44(m) and 2.25(m) |
| 28 | 61.85 t | 3.67(dt, J=10.5, 5) and 3.58(m) |
| 29 | 11.42 q | 1.06(d, J=7.0) |
| 30 | 21.10 q | 1.82(s) |
| 31 | 65.74 t | 3.43(d, J=11.5) and 3.34(d, J=11.5) |
| 32 | 15.30 q | 1.12(s). |

9. The method, according to claim 1, wherein said compound has the following spectroscopic properties:

| Lasonolide E (CDCl3) | | |
|---|---|---|
| Atom No. | $^{13}$C NMR δ mult. | $^1$H NMR δ (mult., J Hz) |
| 1 | 168.55 s | — |
| 2 | 118.34 d | 5.71(d, J=15.5) |
| 3 | 148.32 d | 7.24(dd, J=15.5, 10.5) |
| 4 | 129.01 d | 6.26(dd, J=15.0, 11.0) |
| 5 | 145.10 d | 6.15(dt, J=15.0, 6.0) |
| 6 | 38.52 t | 2.36(m) |
| 7 | 72.48 d | 4.06(m) |
| 8 | 33.80 t | 1.67(m) and 1.53(m) |
| 9 | 70.76 d | 3.99(d, J=2.5) |
| 10 | 38.32 d | 1.64(m) |
| 11 | 68.93 d | 4.81(d, J=9.5) |
| 12 | 124.58 d | 5.46(d, J=9.5) |
| 13 | 138.91 s | — |
| 14 | 129.14 d | 6.59(d, J=16) |
| 15 | 129.69 d | 5.83(dt, J=16, 7.0) |
| 16 | 33.67 t | 2.90(dt, J=13.5, 7.0) and 2.75(m) |
| 17 | 129.01 d | 5.52(m) |
| 18 | 134.16 d | 5.50(m) |
| 19 | 77.08 d | 4.32(m) |
| 20 | 34.98 t | 1.88(t, J=13.0) and 1.42(m) |
| 21 | 74.72 d | 4.96(brs) |
| 22 | 41.26 s | — |
| 23 | 78.03 d | 3.56(dd, J=10, 2.5) |
| 24 | 28.07 t | 2.20(m) and 2.04(m) |
| 25 | 130.77 d | 5.68(dd, J=10.5, 7.5) |
| 26 | 125.05 d | 5.50(m) |
| 27 | 32.50 t | 2.50(2H, m) |
| 28 | 70.25 d | 4.20(dd, J=6.5, 4.5) |
| 29 | 11.40 q | 1.06(d, J=7.0) |
| 30 | 21.08 q | 1.82(s) |
| 31 | 65.66 t | 3.41(d, J=11.5) and 3.33(d, J=11.5) |
| 32 | 15.18 q | 1.12(s) |
| 33 | 174.29 s | — |
| 34 | 61.47 t | 4.23(2H, q, J=7.0) |
| 35 | 14.22 q | 1.30(3H t, J=7.0). |

10. The method, according to claim 1, wherein said compound has the following spectroscopic properties:

| Lasonolide F (in d4-methanol) | | |
|---|---|---|
| Atom No. | $^{13}$C NMR δ mult. | $^1$H NMR δ (mult., J Hz) |
| 1 | 169.05 s | — |
| 2 | 120.72 d | 5.75(d, J=15.2) |
| 3 | 148.02 d | 7.27(dd, J=15.2, 9.7) |
| 4 | 130.54 d* | 6.26(dd, J=15.0, 9.5) |
| 5 | 145.44 d | 6.22(dt, J=15.0, 4.5) |

-continued

Lasonolide F (in d4-methanol)

| Atom No. | $^{13}$C NMR δ mult. | $^{1}$H NMR δ (mult., J Hz) |
|---|---|---|
| 6 | 40.46 t | 2.22(m) |
| 7 | 74.62 d | 4.01(t, J=11) |
| 8 | 34.86 t | 1.63(m) and 1.47(m) |
| 9 | 71.39 d | 3.84(m) |
| 10 | 39.08 d | 1.58(m) |
| 11 | 70.45 d | 4.81(dd, J=10, 2.5) |
| 12 | 125.90 d | 5.40(d, J=9.4) |
| 13 | 139.67 s | — |
| 14 | 130.62 d* | 6.62(d, J=15.9) |
| 15 | 130.89 d* | 5.84(dt, J=15.9, 8.0) |
| 16 | 34.58 t | 2.80(m) and 2.68(m) |
| 17 | 130.10 d* | 5.52(m) |
| 18 | 135.97 d | 5.50(dd, J=10.3, 4.8) |
| 19 | 78.62 d | 4.21(t, J=10.3) |
| 20 | 35.16 t | 1.81(dd, J=12.5, 5) and 1.29(m) |
| 21 | 75.29 d | 5.01(brs) |
| 22 | 41.80 s | — |
| 23 | 80.90 d | 3.65(dd, J=10, 2.5) |
| 24 | 29.39 t | 2.30(m) and 2.04(m) |
| 25 | 130.28 d* | 5.58(m) |
| 26 | 127.68 d | 5.50(m) |
| 27 | 34.15 t | 2.50(m) and 2.30(m) |
| 28 | 73.16 d | 3.90(dd, J=6.7, 4.2) |
| 29 | 11.66 q | 0.99(d, J=7.4) |
| 30 | 20.99 q | 1.80(s) |
| 31 | 66.09 t | 3.40(d, J=11.0) and 3.43(d, J=11.0) |
| 32 | 15.42 q | 1.04(s) |
| 33 | 180.50 s | —. |

11. The method, according to claim 1 wherein said cancer is selected from the group consisting of breast cancer, colon cancer, CNS cancer, liver cancer, lung cancer, leukemia, melanoma, ovarian cancer, uterine cancer, renal cancer, pancreatic cancer and prostate cancer.

12. A pharmaceutical composition comprising a compound having the following structure:

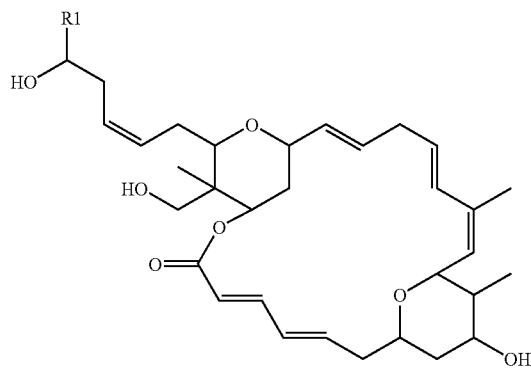

wherein R1=

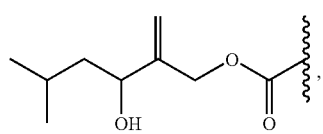

H, COOCH$_2$CH$_3$, or COOH or a salt of said compound wherein said composition further comprises a pharmaceutically acceptable carrier.

13. The composition, according to claim 12, wherein said compound has a structure selected from the group consisting of:

(I)

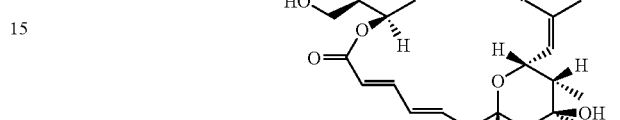
(II)

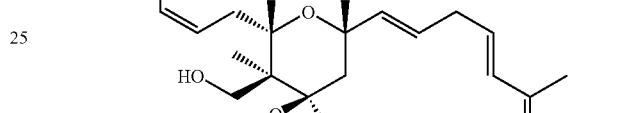
(III)

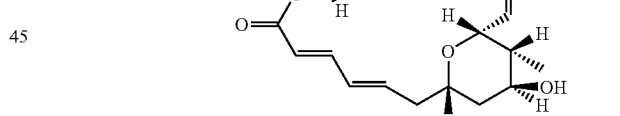
and

(IV)

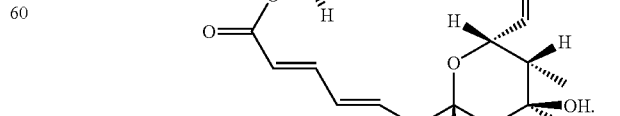

14. The pharmaceutical composition, according to claim 12, comprising a compound having the following structure:

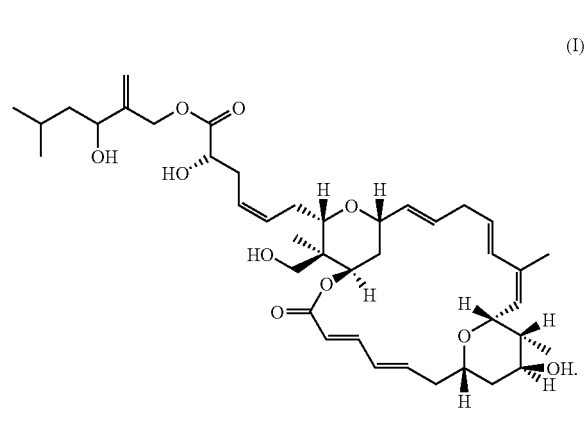

(I)

15. The pharmaceutical composition, according to claim 12, comprising a compound having the following structure:

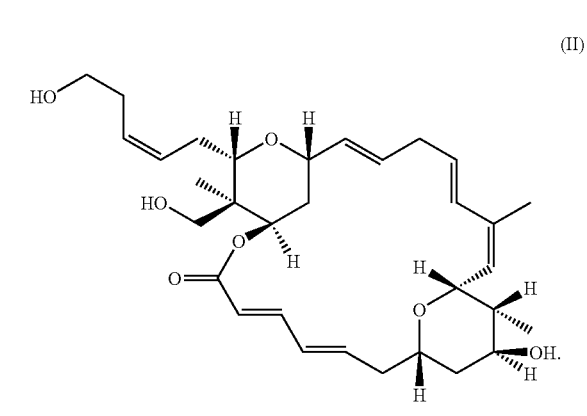

(II)

16. The pharmaceutical composition, according to claim 12, comprising a compound having the following structure:

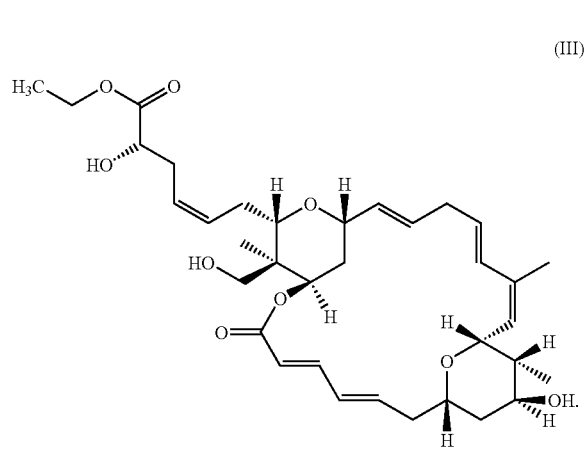

(III)

17. The pharmaceutical composition, according to claim 12, comprising a compound having the following structure:

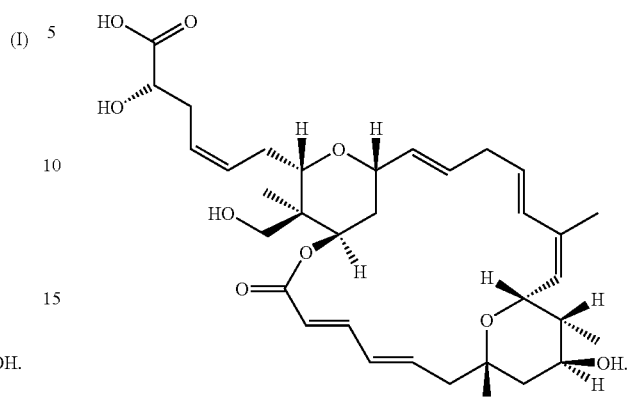

(IV)

18. The composition, according to claim 12, wherein said compound has the following spectroscopic properties:

| Atom No. | $^{13}$C NMR (mult) | $^{1}$H NMR δ (mult., J Hz) |
|---|---|---|
| | Lasonolide C (in CDCL3) | |
| 1 | 168.52 s | — |
| 2 | 118.25 d | 5.69(d, J=15.5) |
| 3 | 148.33 d | 7.24(dd, J=15.5, 11.0) |
| 4 | 128.96 d | 6.26(dd, J=15.0, 11.0) |
| 5 | 145.17 d | 6.15(dt, J=15.0, 6.0) |
| 6 | 38.51 t | 2.35(2H, m) |
| 7 | 72.46 d | 4.05(m) |
| 8 | 33.75 t | 1.66(m) and 1.51(m) |
| 9 | 70.38 d | 3.96(m) |
| 10 | 38.22 d | 1.64(m) |
| 11 | 68.90 d | 4.82(dd, J=9.5, 1.7) |
| 12 | 124.59 d | 5.46(d, J=9.3) |
| 13 | 138.83 s | — |
| 14 | 129.13 d | 6.59(d, J=15.7) |
| 15 | 129.60 d | 5.81(dt, J=15.7, 7.5) |
| 16 | 33.61 t | 2.89(dd, J=12.5, 7.5) and 2.71(m) |
| 17 | 128.81 d | 5.51(m) |
| 18 | 134.28 d | 5.51(m) |
| 19 | 77.14 d | 4.30(m) |
| 20 | 34.89 t | 1.87(dt, J=13.0, <1) and 1.40(m) |
| 21 | 74.68 d | 4.94(brs) |
| 22 | 41.20 s | — |
| 23 | 77.98 d | 3.56(dd, J=9.6, 2.2) |
| 24 | 28.06 t | 2.22(m) and 2.07(m) |
| 25 | 130.84 d | 5.68(dd, J=10.5, 7.5) |
| 26 | 125.03 d | 5.49(m) |
| 27 | 32.48 t | 2.50(m) |
| 28 | 70.64 d | 4.23(m) |
| 29 | 11.36 q | 1.03(d, J=7.0) |
| 30 | 21.04 q | 1.80(s) |
| 31 | 65.58 t | 3.39(d, J=11.5) and 3.32(d, J=11.5) |
| 32 | 15.12 q | 1.08(s) |
| 33 | 173.94 s | — |
| 34 | 64.75 t | 4.76(d, J=13.0) and 4.71(d, J=13.0) |
| 35 | 146.22 s | — |
| 36 | 71.44 d | 4.24(m) |
| 37 | 44.63 t | 1.49(m) and 1.36(m) |
| 38 | 24.63 d | 1.74(m) |
| 39 | 22.03 q | 0.93(d, J=6.5) |
| 40 | 113.94 t | 5.24(s) and 5.15(s) |
| 41 | 23.17 q | 0.93(d, J=6.5). |

19. The composition, according to claim 12, wherein said compound has the following spectroscopic properties:

| Lasonolide D (in CDCl3) | | |
| --- | --- | --- |
| Atom No. | $^{13}$C NMR (mult) | $^1$H NMR δ (mult., J Hz) |
| 1 | 168.53 s | — |
| 2 | 118.39 d | 5.71(d, J=15.5) |
| 3 | 148.29 d | 7.24(dd, J=15.5, 11.0) |
| 4 | 129.05 d | 6.26(dd, J=15.0, 11.0) |
| 5 | 145.08 d | 6.16(dt, J=15.0, 6.0) |
| 6 | 38.55 t | 2.36(m) |
| 7 | 72.49 d | 4.06(m) |
| 8 | 33.81 t | 1.68(m) and 1.53(m) |
| 9 | 70.78 d | 3.99(m) |
| 10 | 38.37 d | 1.60(m) |
| 11 | 68.95 d | 4.81(dd, J=9.4, 1.8) |
| 12 | 124.58 d | 5.46(d, J=9.4) |
| 13 | 138.94 s | — |
| 14 | 129.14 d | 6.58(d, J=16) |
| 15 | 129.74 d | 5.82(dt, J=16, 7.5) |
| 16 | 33.69 t | 2.90(m) and 2.76(m) |
| 17 | 128.87 d | 5.50(m) |
| 18 | 134.20 d | 5.50(m) |
| 19 | 77.17 d | 4.32(dd, J=11, 7.0) |
| 20 | 35.05 t | 1.86(t, J=13.0) |
| 20 | | 1.42(m) |
| 21 | 74.77 d | 4.96(brs) |
| 22 | 41.26 s | — |
| 23 | 77.82 d | 3.59(d, J=10.5) |
| 24 | 28.02 t | 2.33(m) and 2.04(m) |
| 25 | 130.02 d | 5.62(dd, m) |
| 26 | 127.81 d | 5.50(m) |
| 27 | 30.72 t | 2.44(m) and 2.25(m) |
| 28 | 61.85 t | 3.67(dt, J=10.5, 5) and 3.58(m) |
| 29 | 11.42 q | 1.06(d, J=7.0) |
| 30 | 21.10 q | 1.82(s) |
| 31 | 65.74 t | 3.43(d, J=11.5) and 3.34(d, J=11.5) |
| 32 | 15.30 q | 1.12(s). |

20. The composition, according to claim 12, wherein said compound has the following spectroscopic properties:

| Lasonolide E (CDCl3) | | |
| --- | --- | --- |
| Atom No. | $^{13}$C NMR δ mult. | $^1$H NMR δ (mult., J Hz) |
| 1 | 168.55 s | — |
| 2 | 118.34 d | 5.71(d, J=15.5) |
| 3 | 148.32 d | 7.24(dd, J=15.5, 10.5) |
| 4 | 129.01 d | 6.26(dd, J=15.0, 11.0) |
| 5 | 145.10 d | 6.15(dt, J=15.0, 6.0) |
| 6 | 38.52 t | 2.36(m) |
| 7 | 72.48 d | 4.06(m) |
| 8 | 33.80 t | 1.67(m) and 1.53(m) |
| 9 | 70.76 d | 3.99(d, J=2.5) |
| 10 | 38.32 d | 1.64(m) |
| 11 | 68.93 d | 4.81(d, J=9.5) |
| 12 | 124.58 d | 5.46(d, J=9.5) |
| 13 | 138.91 s | — |
| 14 | 129.14 d | 6.59(d, J=16) |
| 15 | 129.69 d | 5.83(dt, J=16, 7.0) |
| 16 | 33.67 t | 2.90(dt, J=13.5, 7.0) and 2.75(m) |
| 17 | 129.01 d | 5.52(m) |
| 18 | 134.16 d | 5.50(m) |
| 19 | 77.08 d | 4.32(m) |
| 20 | 34.98 t | 1.88(t, J=13.0) and 1.42(m) |
| 21 | 74.72 d | 4.96(brs) |
| 22 | 41.26 s | — |
| 23 | 78.03 d | 3.56(dd, J=10, 2.5) |
| 24 | 28.07 t | 2.20(m) and 2.04(m) |
| 25 | 130.77 d | 5.68(dd, J=10.5, 7.5) |
| 26 | 125.05 d | 5.50(m) |
| 27 | 32.50 t | 2.50(2H, m) |
| 28 | 70.25 d | 4.20(dd, J=6.5, 4.5) |
| 29 | 11.40 q | 1.06(d, J=7.0) |
| 30 | 21.08 q | 1.82(s) |

-continued

| Lasonolide E (CDCl3) | | |
| --- | --- | --- |
| Atom No. | $^{13}$C NMR δ mult. | $^1$H NMR δ (mult., J Hz) |
| 31 | 65.66 t | 3.41(d, J=11.5) and 3.33(d, J=11.5) |
| 32 | 15.18 q | 1.12(s) |
| 33 | 174.29 s | — |
| 34 | 61.47 t | 4.23(2H, q, J=7.0) |
| 35 | 14.22 q | 1.30(3H t, J=7.0). |

21. The composition, according to claim 12, wherein said compound has the following spectroscopic properties:

| Lasonolide F (in d4-methanol) | | |
| --- | --- | --- |
| Atom No. | $^{13}$C NMR δ mult. | $^1$H NMR δ (mult., J Hz) |
| 1 | 169.05 s | — |
| 2 | 120.72 d | 5.75(d, J=15.2) |
| 3 | 148.02 d | 7.27(dd, J=15.2, 9.7) |
| 4 | 130.54 d* | 6.26(dd, J=15.0, 9.5) |
| 5 | 145.44 d | 6.22(dt, J=15.0, 4.5) |
| 6 | 40.46 t | 2.22(m) |
| 7 | 74.62 d | 4.01(t, J=11) |
| 8 | 34.86 t | 1.63(m) and 1.47(m) |
| 9 | 71.39 d | 3.84(m) |
| 10 | 39.08 d | 1.58(m) |
| 11 | 70.45 d | 4.81(dd, J=10, 2.5) |
| 12 | 125.90 d | 5.40(d, J=9.4) |
| 13 | 139.67 s | — |
| 14 | 130.62 d* | 6.62(d, J=15.9) |
| 15 | 130.89 d* | 5.84(dt, J=15.9, 8.0) |
| 16 | 34.58 t | 2.80(m) and 2.68(m) |
| 17 | 130.10 d* | 5.52(m) |
| 18 | 135.97 d | 5.50(dd, J=10.3, 4.8) |
| 19 | 78.62 d | 4.21(t, J=10.3) |
| 20 | 35.16 t | 1.81(dd, J=12.5, 5) and 1.29(m) |
| 21 | 75.29 d | 5.01(brs) |
| 22 | 41.80 s | — |
| 23 | 80.90 d | 3.65(dd, J=10, 2.5) |
| 24 | 29.39 t | 2.30(m) and 2.04(m) |
| 25 | 130.28 d* | 5.58(m) |
| 26 | 127.68 d | 5.50(m) |
| 27 | 34.15 t | 2.50(m) and 2.30(m) |
| 28 | 73.16 d | 3.90(dd, J=6.7, 4.2) |
| 29 | 11.66 q | 0.99(d, J=7.4) |
| 30 | 20.99 q | 1.80(s) |
| 31 | 66.09 t | 3.40(d, J=11.0) and 3.43(d, J=11.0) |
| 32 | 15.42 q | 1.04(s) |
| 33 | 180.50 s | —. |

22. A method for inhibiting the growth of *candida albicans*, said method comprising applying to the *candida albicons* a compound having the following structure:

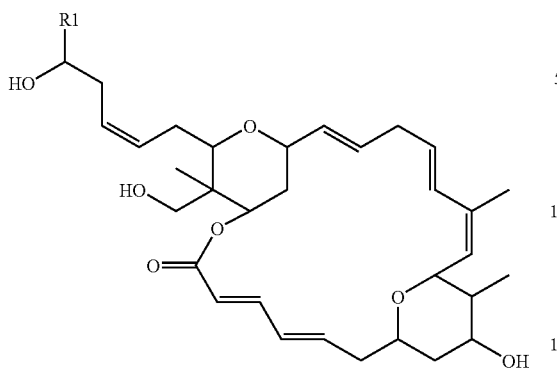

wherein R1=

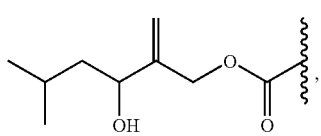

H, COOCH$_2$CH$_3$, or COOH;
or a salt of said compound.

23. The method, according to claim 22, wherein said compound is selected from the group consisting of:

(I)

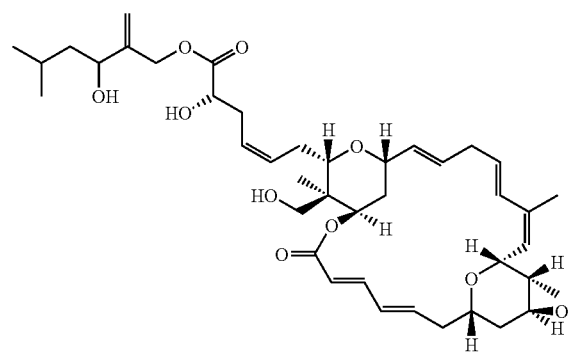

and (IV)

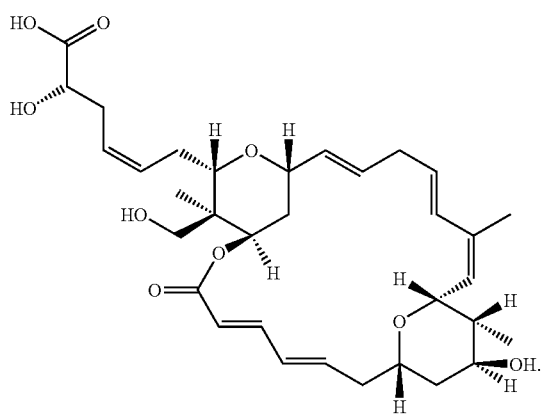

24. The method, according to claim 22, wherein the compound has the following structure:

(I)

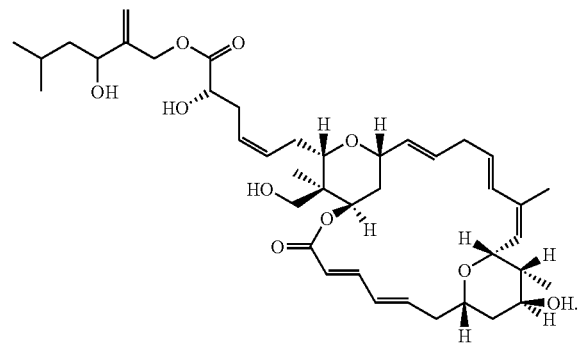

25. The method, according to claim 22, wherein the compound has the following structure:

(IV)

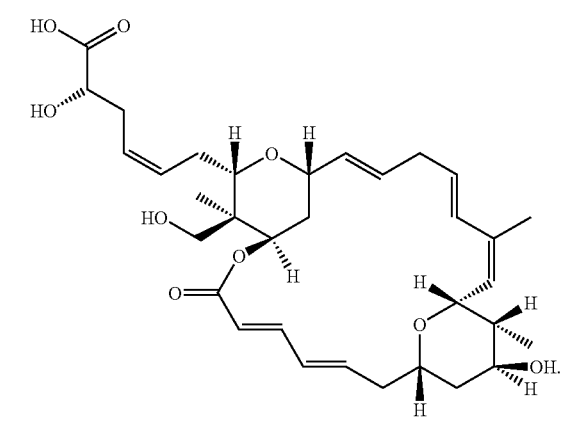

26. The method, according to claim 22, wherein said compound has the following spectroscopic properties:

| | Lasonolide C (in CDCL3) | |
|---|---|---|
| Atom No. | $^{13}$C NMR (mult) | $^1$H NMR δ (mult., J Hz) |
| 1 | 168.52 s | — |
| 2 | 118.25 d | 5.69(d, J=15.5) |
| 3 | 148.33 d | 7.24(dd, J=15.5, 11.0) |
| 4 | 128.96 d | 6.26(dd, J=15.0, 11.0) |
| 5 | 145.17 d | 6.15(dt, J=15.0, 6.0) |
| 6 | 38.51 t | 2.35(2H, m) |
| 7 | 72.46 d | 4.05(m) |
| 8 | 33.75 t | 1.66(m) and 1.51(m) |
| 9 | 70.38 d | 3.96(m) |
| 10 | 38.22 d | 1.64(m) |
| 11 | 68.90 d | 4.82(dd, J=9.5, 1.7) |
| 12 | 124.59 d | 5.46(d, J=9.3) |
| 13 | 138.83 s | — |
| 14 | 129.13 d | 6.59(d, J=15.7) |
| 15 | 129.60 d | 5.81(dt, J=15.7, 7.5) |
| 16 | 33.61 t | 2.89(dd, J=12.5, 7.5) and 2.71(m) |
| 17 | 128.81 d | 5.51(m) |
| 18 | 134.28 d | 5.51(m) |
| 19 | 77.14 d | 4.30(m) |
| 20 | 34.89 t | 1.87(dt, J=13.0, <1) and 1.40(m) |

-continued

Lasonolide C (in CDCL3)

| Atom No. | 13C NMR (mult) | 1H NMR δ (mult., J Hz) |
|---|---|---|
| 21 | 74.68 d | 4.94(brs) |
| 22 | 41.20 s | — |
| 23 | 77.98 d | 3.56(dd, J=9.6, 2.2) |
| 24 | 28.06 t | 2.22(m) and 2.07(m) |
| 25 | 130.84 d | 5.68(dd, J=10.5, 7.5) |
| 26 | 125.03 d | 5.49(m) |
| 27 | 32.48 t | 2.50(m) |
| 28 | 70.64 d | 4.23(m) |
| 29 | 11.36 q | 1.03(d, J=7.0) |
| 30 | 21.04 q | 1.80(s) |
| 31 | 65.58 t | 3.39(d, J=11.5) and 3.32(d, J=11.5) |
| 32 | 15.12 q | 1.08(s) |
| 33 | 173.94 s | — |
| 34 | 64.75 t | 4.76(d, J=13.0) and 4.71(d, J=13.0) |
| 35 | 146.22 s | — |
| 36 | 71.44 d | 4.24(m) |
| 37 | 44.63 t | 1.49(m) and 1.36(m) |
| 38 | 24.63 d | 1.74(m) |
| 39 | 22.03 q | 0.93(d, J=6.5) |
| 40 | 113.94 t | 5.24(s) and 5.15(s) |
| 41 | 23.17 q | 0.93(d, J=6.5). |

27. The method, according to claim 1, wherein said compound has the following spectroscopic properties:

Lasonolide F (in d4-methanol)

| Atom No. | 13C NMR δ mult. | 1H NMR δ (mult., J Hz) |
|---|---|---|
| 1 | 169.05 s | — |
| 2 | 120.72 d | 5.75(d, J=15.2) |
| 3 | 148.02 d | 7.27(dd, J=15.2, 9.7) |
| 4 | 130.54 d* | 6.26(dd, J=15.0, 9.5) |
| 5 | 145.44 d | 6.22(dt, J=15.0, 4.5) |

-continued

Lasonolide F (in d4-methanol)

| Atom No. | 13C NMR δ mult. | 1H NMR δ (mult., J Hz) |
|---|---|---|
| 6 | 40.46 t | 2.22(m) |
| 7 | 74.62 d | 4.01(t, J=11) |
| 8 | 34.86 t | 1.63(m) and 1.47(m) |
| 9 | 71.39 d | 3.84(m) |
| 10 | 39.08 d | 1.58(m) |
| 11 | 70.45 d | 4.81(dd, J=10, 2.5) |
| 12 | 125.90 d | 5.40(d, J=9.4) |
| 13 | 139.67 s | — |
| 14 | 130.62 d* | 6.62(d, J=15.9) |
| 15 | 130.89 d* | 5.84(dt, J=15.9, 8.0) |
| 16 | 34.58 t | 2.80(m) and 2.68(m) |
| 17 | 130.10 d* | 5.52(m) |
| 18 | 135.97 d | 5.50(dd, J=10.3, 4.8) |
| 19 | 78.62 d | 4.21(t, J=10.3) |
| 20 | 35.16 t | 1.81(dd, J=12.5, 5) and 1.29(m) |
| 21 | 75.29 d | 5.01(brs) |
| 22 | 41.80 s | — |
| 23 | 80.90 d | 3.65(dd, J=10, 2.5) |
| 24 | 29.39 t | 2.30(m) and 2.04(m) |
| 25 | 130.28 d* | 5.58(m) |
| 26 | 127.68 d | 5.50(m) |
| 27 | 34.15 t | 2.50(m) and 2.30(m) |
| 28 | 73.16 d | 3.90(dd, J=6.7, 4.2) |
| 29 | 11.66 q | 0.99(d, J=7.4) |
| 30 | 20.99 q | 1.80(s) |
| 31 | 66.09 t | 3.40(d, J=11.0) and 3.43(d, J=11.0) |
| 32 | 15.42 q | 1.04(s) |
| 33 | 180.50 s | —. |

28. The method, according to claim 1, wherein said cancer is selected from pancreatic cancer, colon cancer, lung cancer, leukemia and ovarian cancer.

29. The method, according to claim 28, wherein said cancer is selected from pancreatic cancer and colon cancer.

* * * * *

UNITED STATES PATENT AND TRADEMARK OFFICE
CERTIFICATE OF CORRECTION

PATENT NO. : 7,521,474 B2  Page 1 of 4
APPLICATION NO. : 11/494229
DATED : April 21, 2009
INVENTOR(S) : Amy E. Wright et al.

It is certified that error appears in the above-identified patent and that said Letters Patent is hereby corrected as shown below:

Column 6,
Line 59, Structure I,

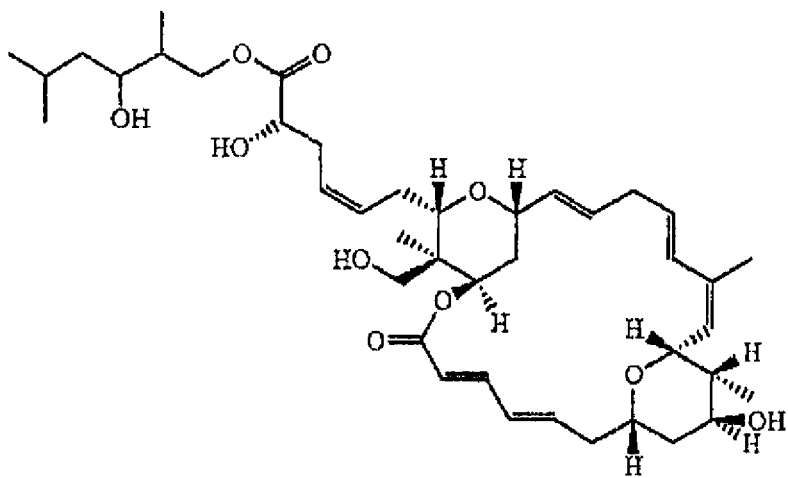

Should read:

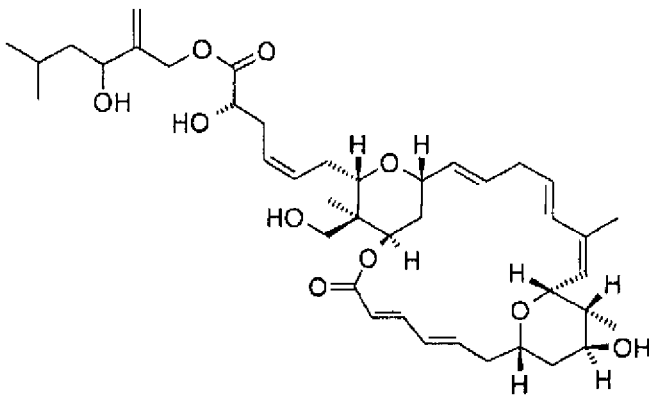

UNITED STATES PATENT AND TRADEMARK OFFICE
CERTIFICATE OF CORRECTION

PATENT NO.        : 7,521,474 B2
APPLICATION NO.   : 11/494229
DATED             : April 21, 2009
INVENTOR(S)       : Amy E. Wright et al.

It is certified that error appears in the above-identified patent and that said Letters Patent is hereby corrected as shown below:

Column 16,
Line 45, Structure I,

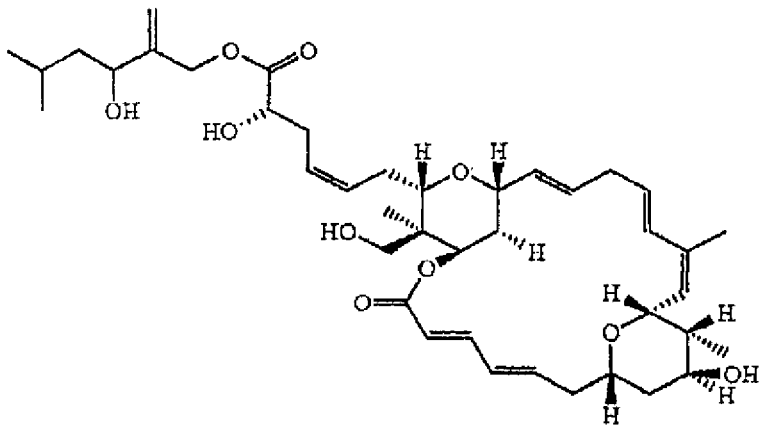

Should read:

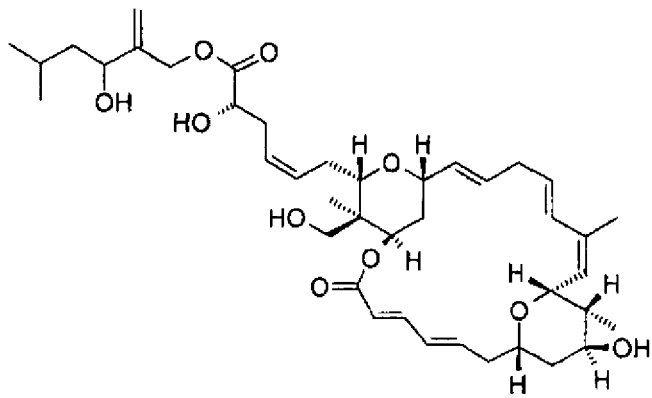

UNITED STATES PATENT AND TRADEMARK OFFICE
CERTIFICATE OF CORRECTION

PATENT NO. : 7,521,474 B2
APPLICATION NO. : 11/494229
DATED : April 21, 2009
INVENTOR(S) : Amy E. Wright et al.

It is certified that error appears in the above-identified patent and that said Letters Patent is hereby corrected as shown below:

Column 22,
Line 8, Structure I,

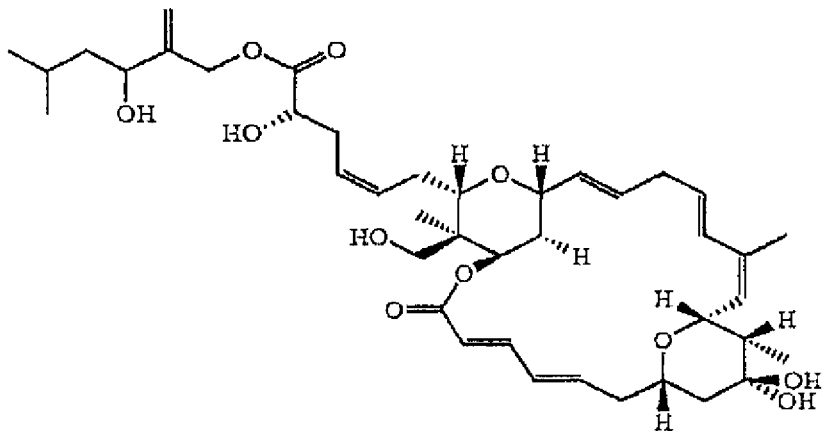

UNITED STATES PATENT AND TRADEMARK OFFICE
CERTIFICATE OF CORRECTION

PATENT NO. : 7,521,474 B2
APPLICATION NO. : 11/494229
DATED : April 21, 2009
INVENTOR(S) : Amy E. Wright et al.

It is certified that error appears in the above-identified patent and that said Letters Patent is hereby corrected as shown below:

Should read:

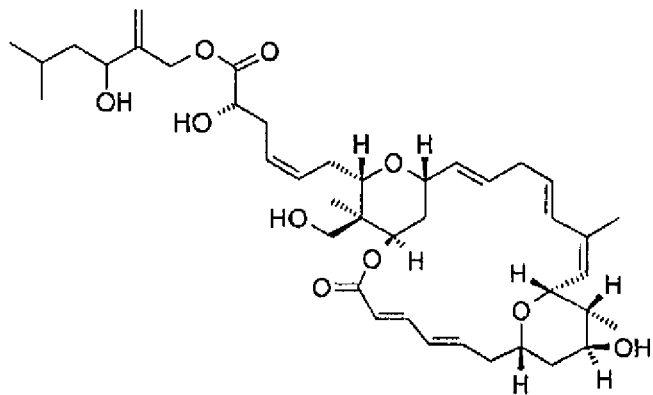

(I)

Signed and Sealed this

Tenth Day of November, 2009

David J. Kappos
*Director of the United States Patent and Trademark Office*